United States Patent
Patel et al.

(12)

(10) Patent No.: US 6,758,867 B2
(45) Date of Patent: Jul. 6, 2004

(54) GRADUAL PERMANENT COLORING OF HAIR USING DYE INTERMEDIATES IN A SHAMPOO BASE

(75) Inventors: Jitendra Patel, Fox River Grove, IL (US); Gerald Patrick Newell, Hoffman Estates, IL (US); Elizabeth Kim, Morton Grove, IL (US); Fe P Pascual, Elk Grove Village, IL (US); Margie Fowler, Elgin, IL (US)

(73) Assignee: Unilever Home & Personal Care USA, Division of Conopco, Inc., Chicago, IL (US)

( * ) Notice: Subject to any disclaimer, the term of this patent is extended or adjusted under 35 U.S.C. 154(b) by 175 days.

(21) Appl. No.: 10/034,511

(22) Filed: Dec. 28, 2001

(65) Prior Publication Data

US 2003/0140428 A1 Jul. 31, 2003

(51) Int. Cl.$^7$ ................................................ A61K 7/13
(52) U.S. Cl. ................ 8/405; 8/406; 8/408; 8/410; 8/411; 8/412; 8/421; 8/435; 8/611; 8/540; 8/580; 8/581; 8/606
(58) Field of Search .................. 8/405, 406, 408, 8/410, 411, 412, 421, 435, 611, 540, 580, 581, 606

(56) References Cited

U.S. PATENT DOCUMENTS

| | | | |
|---|---|---|---|
| 3,816,615 A | 6/1974 | Zeffren et al. ............... 424/62 |
| 3,912,446 A | 10/1975 | Zviak et al. ................. 8/10.1 |
| 3,931,912 A | 1/1976 | Hsiung ....................... 222/94 |
| 4,096,243 A | 6/1978 | Feinland et al. ............. 424/62 |
| 4,104,021 A | * 8/1978 | Lapidus et al. .............. 8/10.2 |
| 4,297,098 A | 10/1981 | Dasher et al. ............... 8/412 |
| 4,369,037 A | 1/1983 | Matsunaga et al. ........... 8/127 |
| 4,402,700 A | 9/1983 | Feinland et al. ............. 8/416 |
| 4,529,404 A | 7/1985 | Feinland et al. ............. 8/406 |
| 4,566,876 A | 1/1986 | Brown et al. ................ 8/411 |
| 4,656,043 A | 4/1987 | Hawkins et al. ............. 424/70 |
| 4,749,565 A | 6/1988 | Grollier ..................... 424/70 |
| 4,925,666 A | 5/1990 | Decker, Jr. et al. ......... 424/401 |
| 5,008,105 A | 4/1991 | Grollier et al. ............. 424/70 |
| 5,049,377 A | 9/1991 | Lamb et al. ................. 424/70 |
| 5,064,441 A | 11/1991 | Kawase et al. ............... 8/405 |
| 5,089,257 A | 2/1992 | Schrader ..................... 424/70 |
| 5,102,655 A | 4/1992 | Yoshihara et al. ........... 424/70 |
| 5,116,388 A | 5/1992 | Brooks ....................... 8/405 |
| 5,130,124 A | 7/1992 | Merianos et al. ............ 424/53 |
| 5,221,286 A | 6/1993 | Singleton et al. ............ 8/406 |
| 5,376,146 A | * 12/1994 | Casperson et al. ............ 8/408 |
| 5,393,305 A | 2/1995 | Cohen et al. ................. 8/406 |
| 5,554,197 A | 9/1996 | Assini et al. ................. 8/405 |
| 5,556,615 A | 9/1996 | Janchitraponvej et al. ....................... 424/70.11 |
| 5,560,750 A | 10/1996 | Crews et al. ................. 8/431 |
| 5,730,966 A | 3/1998 | Torgerson et al. ........ 424/70.11 |
| 5,849,042 A | 12/1998 | Lim et al. .................... 8/408 |
| 5,942,216 A | 8/1999 | Herb et al. ............... 424/70.28 |
| 5,968,486 A | 10/1999 | Newell et al. ................ 424/62 |
| 5,993,491 A | 11/1999 | Lim et al. .................... 8/409 |
| 6,022,381 A | 2/2000 | Dias et al. ................... 8/406 |
| 6,074,438 A | 6/2000 | Lim et al. .................... 8/409 |
| 6,082,588 A | 7/2000 | Markey et al. .............. 222/137 |
| 6,143,286 A | 11/2000 | Bhambhani et al. ....... 424/70.1 |
| 6,309,426 B1 | 10/2001 | Dias et al. ................... 8/407 |
| 2003/0028979 A1 * | 2/2003 | Duffer et al. ................. 8/406 |

FOREIGN PATENT DOCUMENTS

| | | | |
|---|---|---|---|
| DE | 2217388 | 11/1972 | |
| DE | 100 51 774 | 10/2000 | |
| EP | 1 289 712 | * 9/1972 | ............. D06P/1/32 |
| EP | 0046543 A2 | 3/1982 | |
| EP | 0 146 350 | 12/1984 | |
| EP | 0 823 250 | 12/1996 | |
| FR | 2 802 089 | 12/1999 | |
| GB | 1289712 | 9/1972 | |
| WO | 00/10515 | 3/2000 | |
| WO | 01/76545 | 10/2001 | |
| WO | 01/76546 | 10/2001 | |
| WO | 02/074266 A2 | 9/2002 | |

OTHER PUBLICATIONS

Copending application: Applicant: Newell et al., Ser. No.: 09/558,235, Filed: Apr. 24, 2000, For: A Composition for Lightening and Highlighting Hair, UNUS No.: 97–0263–A–HC.

(List continued on next page.)

Primary Examiner—Brian P. Mruk
Assistant Examiner—Eisa Elhilo
(74) Attorney, Agent, or Firm—Milton L. Honig

(57) ABSTRACT

A method for permanently dyeing hair which comprises subjecting said hair to a number of treatments, having a set time interval between each two consecutive such treatments, wherein each treatment comprises steps a.) and b.) below:

a.) contacting said hair, for a period of about 5 seconds to about 5 minutes with a recently made mixture of:
part ai: oxidative dye intermediates in a shampoo base at alkaline pH and wherein part ai optionally has about 0.01 to about 5.0% of a conditioning agent; and part ai optionally has about 0.01 to about 10.0% of a structurant;
part aii: an oxidative compound in a shampoo base at acidic pH and wherein part ai optionally has about 0.01 to about 5.0% of a conditioning agent; and part ai optionally has about 0.01 to about 10.0% of a structurant;
with the proviso that at least one of part ai and part aii has about 0.01 to about 5.0% of a conditioning agent; and part aii optionally has about 0.01 to about 10.0% of a structurant;

b.) rinsing said mixture from said hair with water;

and wherein said number of treatments is between about 2 to about 30; and wherein said set time interval between each two consecutive treatments is between about 8 hours and 30 days.

34 Claims, No Drawings

OTHER PUBLICATIONS

Copending application: Applicant: Patel et al., Ser. No. 09/811,920, Filed: Mar. 19, 2001, For: Method and Composition for Gradual Permanent Coloring of Hair, UNUS No.: Y2–0530–HC, Case No.: J6691(C).

International Search Report Application No. PCT/EP 02/13951 mailed Apr. 9, 2003.

Derwent Abstract, XP 002236077 & JP 54 070442 A (Murai Y), (7/79).

* cited by examiner

GRADUAL PERMANENT COLORING OF HAIR USING DYE INTERMEDIATES IN A SHAMPOO BASE

BACKGROUND OF THE INVENTION

The present invention relates to a method for the permanent coloring of hair with cleansing and with minimized hair damage.

Most hair coloring products fall under three major groupings:

1. Temporary hair color.
2. Semi permanent hair color.
3. Permanent hair color.

Temporary hair color is a leave on product that causes minimal damage to the hair. However, temporary hair color causes stains, and leaches out under rain or with perspiration. Temporary color washes out with the next shampoo. Temporary hair color also does not give any control to the consumer over the amount of color deposited or the permanency of the color supplied. Temporary hair color does not result in a wide variety of colors and it has only a limited appeal.

Semi-permanent hair color comes as a rinse, and it causes minimal damage to the hair. However, semi-permanent hair color washes out to some degree with each shampoo and washes out completely within about 4 to 6 shampoos. Semi permanent hair color does not give the consumer any control regarding the amount of color deposited or the permanency of the color. Semi-permanent hair color has limited popularity with consumers.

Permanent hair color generally comes in two parts: a dye solution and a developer solution. Because of the damaging nature of conventional permanent hair color treatments, most permanent home coloring products come with a post treatment conditioner. In a permanent hair coloring treatment, the dye solution and the developer solution are mixed and then applied to the hair, which is then left for about 25 to about 35 minutes. The hair is then rinsed with water, treated with a post treatment conditioner, and then rinsed again with water.

The application of the dye solution and the developer solution affords permanent hair coloring. However, this method does not provide any conditioning benefit. The conditioning benefit comes through application of the post treatment conditioner, and it is only temporary. The conditioning benefit is lost with the next shampoo. Moreover, with permanent hair coloring treatments, shampooing the hair is usually not recommended after said treatments. Thus, hair is left feeling dirty, and can stain towels and pillows.

Permanent hair coloring products need to be applied every four to six weeks since hair grows out of the scalp at the rate of approximately one half inch per month. Each permanent hair coloring application causes damage to the hair, and that damage is cumulative. Hair coloring touch ups after the initial treatment would also damage hair more.

It would be desirable to develop a method for permanently coloring hair which gives hair a soft clean feel, and minimizes the damage caused to hair by the coloring process. The present invention provides such a method.

Conventional hair coloring products cannot be used safely in the shower. It is an object of this invention to develop a method for permanently coloring hair, which can be carried out safely in the shower, for example. It is also an object of the invention to provide a method for permanently coloring hair, wherein the user has control of the amount of permanent or durable color deposited without hair damage. It is also an object of the invention to provide a method for permanently coloring hair wherein the user can employ the product as her daily hair care product to avoid new outgrowth of uncolored hair. It is also an object of the invention to provide a method for permanently coloring hair wherein said method involves less mess and difficulty than conventional permanent hair coloring methods. It is also an object of the invention to provide a method for permanently coloring hair wherein said method brings about gradual color changes with each application. Since gradual color changes are to occur, such a method would be virtually mistake free because the consumer could stop or alter the coloring method if she did not like the course the hair coloring was initially taking. It is also an object of the invention to provide a method for permanently coloring hair wherein the amount of hair coloring composition employed can be varied from application to application in order to adjust the hair coloring results.

These and other aspects of this invention will become evident by a detailed description of the invention given below.

Patents related to the field of this invention are as follows:

U.S. Pat. No. 4,104,021 which discloses a process in which human hair is dyed in successive treatments at selected intervals with oxidation colors (aromatic primary amines and amino phenols) admixed in each treatment with an oxidizing agent ($H_2O_2$ or a derivative thereof)—the quantity of oxidation colorant applied in each treatment being substantially the same and the quantity of oxidizing agent being increased from the first to the last treatment to effect a gradual increase in depth of shade—the mixture being allowed to remain on the hair for substantially the same time in each treatment, followed by removal by rinsing.

U.S. Pat. No. 4,529,404 discloses an autoxidizable hair dye preparation capable of coloring or darkening hair when applied thereto and exposed to the atmosphere comprising a mixture of (I) at least one p-phenylene diamine compound, or An acid addition salt thereof, and (II) at least one 1,2,4-benzenetriol compound, each compound optionally containing nuclearly substituted $C_{1-4}$ alkyl, alkoxy, hydroxyalkyl or halogen. The preparation is preferably applied and exposed to the atmosphere repeatedly until the desired degree of darkening or color build-up is attained.

The preparations of this invention may also contain known additives or assistants such as hair grooming agents, for example quaternized vinyl pyrrolidone copolymers, carboxyvinyl polymers and the like, plasticizers, thickeners, slip and wetting agents such as silicone copolymer, foam boosters, preservatives, perfumes and the like.

U.S. Pat. No. 5,968,486 describes a shampoo composition for lightening and highlighting hair which comprises (i) a peroxygen compound; and
(ii) an anionic sulfonate;

said composition having a pH less than 5. There is also described an invention directed to a method for lightening and highlighting hair which comprises shampooing the hair with a lightening and highlighting effective amount of a composition of the invention.

U.S. Pat. No. 6,274,126 discloses a hair conditioning composition for conditioning, lightening, and highlighting hair, which comprises i) peroxygen compound, and
ii) a conditioning agent, said composition having a pH of 5 or less.

U.S. patent application No. 2003/0051297 A1 discloses a method for permanently dyeing hair which comprises subjecting said hair to a number of treatments, having a set time interval between each two consecutive such treatments, wherein each treatment comprises steps a.) and b.) below:

a.) contacting said hair for a period of about 5 seconds to about 5 minutes with a recently made mixture of:
i.) an alkaline composition comprising a dye intermediate in a shampoo base or in a conditioner base; and
ii.) an acidic composition comprising an oxidating compound in a shampoo base or in a conditioner base;
b.) rinsing said mixture from said hair with water;

with the proviso that when a conditioner base is present in a.) i.) above, an independently selected conditioner base is also present in a.) ii.) above; and when a shampoo base is present in a.) i.) above, an independently selected shampoo base is also present in a.) ii.) above;

and wherein said number of treatments is between about 2 to about 30; and wherein said set time interval between each two consecutive treatments is between about 8 hours and 30 days, is described.

SUMMARY OF THE INVENTION

The present invention relates to a method for achieving permanent desired hair color change through the use of daily hair care compositions. The daily hair care compositions comprise a mixture of two compositions: part ai and part aii as described just below:

part ai: oxidative hair dyes in a shampoo base at alkaline pH; and wherein part ai optionally has about 0.01 to about 5.0% of a conditioning agent, and optionally has about 0.01 to about 10.0% of a structurant;

part aii: an oxidative compound in a shampoo base at acidic pH and wherein part aii optionally has about 0.01 to about 5.0% of a conditioning agent; and optionally has about 0.01 to about 10.0% of a structurant;

with the proviso that at least one of part ai and part aii has about 0.01 to about 5.0% of a conditioning agent; and at least one of part ai and part aii optionally has about 0.01 to about 10.0% of a structurant.

The present invention also relates to a method for permanently coloring hair which comprises applying to the hair compositions of the invention in the manner described herein.

DETAILED DESCRIPTION OF THE INVENTION

As used herein % means weight % unless otherwise indicated. When used herein % refers to weight % as compared to the total weight percent of the composition that is being discussed. For example, when % is used to discuss the amount of an ingredient that is in part ai, this means to weight % as compared to the total weight of part ai. When to weight % of the mixture of part ai and part aii is mentioned, this means the weight % as compared to the total weight the mixture of part ai and part aii. When the ratio of part ai to part aii is discussed this means the weight to weight ratio. As used herein the term "recently" means within a very short interval of time such as within a few seconds or minutes, such as within 0.01 seconds to 120 seconds, or within 0.1 seconds to 60 seconds, or within 0.5 second to within 30 second or within 2 seconds to within 20 seconds. Compositions of the invention may be made by means which are known in the art or which are analogous to those which are know in the art. Ingredients which are included in compositions of the invention are known in the art or may be made by means which are known in the art.

The daily hair care compositions comprise a mixture of two compositions: part ai and part aii wherein part ai: comprises oxidative hair dyes in a shampoo base at alkaline pH; and wherein part ai optionally has about 0.01 to about 5.0% of a conditioning agent, and optionally has about 0.01 to about 10.0% of a structurant;

part aii: comprises an oxidative compound in a shampoo base at acidic pH and wherein part aii optionally has about 0.01 to about 5.0% of a conditioning agent; and optionally has about 0.01 to about 10.0% of a structurant;

with the proviso that at least one of part ai and part aii has about 0.01 to about 5.0% of a conditioning agent; and at least one of part ai and part aii optionally has about 0.01 to about 10.0% of a structurant.

Part ai may comprise from
a) about 0.1 to about 99.9% of an aqueous shampoo base, wherein the shampoo or cleansing or surfactant agent within said shampoo base comprises from about 10 to about 50% of the total composition;
b) about 0.1 to about 5% of oxidative hair dyes;
c) about 0.1 to about 5% of a coupling compound;
and optionally has about 0.01 to about 5.0% of a conditioning agent, more preferably about 1.0% to about 4.0% of a conditioning agent;
and optionally has about 0.01 to about 10.0% of a structurant; more preferably about 1.0% to about 8.0%.

More preferably, part ai can comprise from
a) about 0.1 to about 99.9% of an aqueous shampoo base, wherein the shampoo or cleansing or surfactant agent within said shampoo base is about 10 to about 50% of a shampooing agent;
b) about 0.1 to about 1.0% of oxidative hair dyes;
c) about 0.1 to about 1% coupling compound;
and optionally has about 0.01 to about 5.0% of a conditioning agent, more preferably about 1.0% to about 4.0% of a conditioning agent;
and optionally has about 0.01 to about 10.0% of a structurant; more preferably about 1.0% to about 8.0%.

Part aii may comprise from:
a) about 1 to about 99% of a shampoo base agent comprising about 10 to about 50% of a shampooing agent; and
b) about 2% to about 5% of an oxidizing compound;
and optionally has about 0.01 to about 5.0% of a conditioning agent, more preferably about 1.0% to about 4.0% of a conditioning agent;
and optionally has about 0.01 to about 10.0% of a structurant; more preferably about 1.0% to about 8.0%.

Part aii more preferably can comprise from:
a) about 1 to about 99% of a shampoo base agent comprising about 10 to about 50% of a shampooing agent; and
b) about 2 to about 5% of an oxidizing compound.
and optionally has about 0.01 to about 5.0% of a conditioning agent;
and optionally has about 0.01 to about 10.0% of a structurant.

Shampooing compositions of the present invention can comprise a mixture of part ai and part aii wherein:
Part ai can comprise:
about 0.1% to about 99.9% of a shampooing base, which comprises about 10% to about 50% of a shampooing agent based upon the total composition; oxidative hair dyes; and optionally has about 0.01 to about 5.0% of a conditioning agent;

and optionally has about 0.01 to about 10.0% of a structurant.

a) about 0.1% to about 1% of a dye; and b) a volatile silicone;

Part aii can comprise:

a) about 1 to about 5% of a shampooing base;

b) about 1 to about 5% of an oxidative compound;

and optionally has about 0.01 to about 5.0% of a conditioning agent;

and optionally has about 0.01 to about 10.0% of a structurant.

In the compositions of the invention part ai is mixed with part aii to form the final hair coloring composition that is applied to the hair. It is understood that at least one of part aii and part aii as described above has about 0.01 to about 5.0% of a conditioning agent.

In the compositions of the invention part ai is mixed with part aii to form the final hair coloring composition that is applied to the hair. It is understood that at least one of part aii and part aii as described above has about 0.01 to about 5.0% of a conditioning agent. Part ai and part aii can be mixed in about a 1.2:0.8 to about 0.8:1.2 ratio, respectively, more preferably about a 1:1 ratio.

A shampooing composition of the invention may be a composition as described just above, which further comprises in part ai, part aii; or part ai and part aii, a thickener.

What follows is a description of the ingredients that can be included in the compositions of the present invention.

Oxidative Hair Dyes and Hair Coloring Agents

The part ai compositions of the present invention include one or more oxidative hair dyes or hair coloring agents. These oxidative hair coloring dyes or hair coloring agents are present in compositions of the present invention which have a shampoo base. Such oxidative hair coloring dyes or hair coloring agents are used in combination with the oxidizing systems of the present invention to formulate permanent hair dye compositions. Part ai can also comprise about 0.01 to about 5.0% of a conditioning agent as described above.

Permanent hair coloring dye compositions as defined herein are compositions, which once applied to the hair, are substantially resistant to washout.

Oxidative Dyes

The dye forming intermediates used in oxidative hair coloring dyes of the invention can be aromatic diamines, aminophenols and their derivatives. These dye forming intermediates can be classified as: primary and secondary intermediates, couplers and modifiers, and nitro dyes. Primary intermediates are chemical compounds, which by themselves will form a dye upon oxidation. Secondary intermediates, also known as color modifiers or couplers, are used with other intermediates for specific color effects or to stabilize the color. Nitro dyes are unique in that they are direct dyes, which do not require oxidation to dye the hair.

The oxidation dye intermediates, which are suitable for, use in the compositions and processes herein include aromatic diamines, polyhydric phenols, aminophenols and derivatives of these aromatic compounds (e.g., N-substituted derivatives of the amines, and ethers of the phenols). Primary oxidation dye intermediates are generally colorless molecules prior to oxidation. The oxidation dye color is generated when the primary intermediate is 'activated' and subsequently joined with a secondary intermediate (coupling agent), which is also generally colorless, to form a colored, conjugated molecule. In general terms, oxidation hair dye precursors or intermediates include those monomeric materials which, on oxidation, form oligomers or polymers having extended conjugated systems of electrons in their molecular structure. Because of the new electronic structure, the resultant oligomers and polymers exhibit a shift in their electronic spectra to the visible range and appear colored. For example, oxidation dye precursors capable of forming colored polymers include materials such as aniline, which has a single functional group and which, on oxidation, forms a series of conjugated imines and quinoid dimers, trimers, etc. ranging in color from green to black. Compounds such as p-phenylenediamine, which has two functional groups, are capable of oxidative polymerization to yield higher molecular weight colored materials having extended conjugated electron systems. Color modifiers (couplers), such as those detailed hereinafter, are preferably used in conjunction with the oxidation dye precursors herein and are thought to interpose themselves in the colored polymers during their formation and to cause shifts in the electronic spectra thereof, thereby resulting in slight color changes. A representative list of oxidation dye precursors suitable for use herein is found in Sagarin, "Cosmetic Science and Technology", Interscience, Special Edition, Volume 2, pages 308 to 310 which is herein incorporated by reference.

It is to be understood that the oxidizing aids of the present invention are suitable for use (in combination with a source of peroxide as detailed herein) with all manner of oxidation dye precursors and color modifiers and that the precursors detailed below are only by way of example and are not intended to limit the compositions and processes herein.

The typical aromatic diamines, polyhydric phenols, aminophenols, and derivatives thereof, described above as primary dye precursors can also have additional substituents on the aromatic ring, e.g. halogen, aldehyde, carboxylic additional substituents on the amino nitrogen and on the phenolic oxygen, e.g. substituted and unsubstituted alkyl and aryl groups.

The hair coloring compositions of the present invention may, in addition to the essential oxidative hair-coloring agents, optionally include non-oxidative and other dye materials. Optional non-oxidative and other dyes suitable for use in the hair coloring compositions and processes according to the present invention include semi-permanent, temporary and other dyes. Non-oxidative dyes as defined herein include the so-called 'direct action dyes', metallic dyes, metal chelate dyes, fiber reactive dyes and other synthetic and natural chemicals. See Chemical and Physical Behaviour of Human Hair' 3rd Edn. by Clarence Robbins (pp 250–259); 'The Chemistry and Manufacture of Cosmetics'. Volume IV. 2nd Edn. Maison G. De dyes. Various types of non-oxidative dyes are detailed in: 'Navarre at chapter 45 by G. S. Kass (pp 841–920); 'Cosmetics: Science and Technology' 2nd Edn, Vol II Balsam Sagarin; Chapter 23 by F. E. Wall (pp 279–343); 'The Science of Hair Care' edited by C. Zviak, Chapter 7 (pp 235–261) and 'Hair Dyes', J. C. Johnson, Noyes Data Corp., Park Ridge, U.S.A. (1973), (pp 3–91 and 113–139).

Specific hair dyes which may be included in the compositions of the invention include m-aminophenol, p-phenylene diamine, p-toluenediamine; p-phenylenediamine; 2-chloro-p-phenylenediamine; N-phenyl-p-phenylenediamine; N-2-methoxyethyl-p-phenylenediamine; N,N-bis-(hydroxyethyl)-p-phenylenediamine; 2-hydroxymethyl-p-phenylenediamine;

2-hydroxyethyl-p-phenylenediamine; 4,4'-diaminodiphenylamine; 2,6-dimethyl-p-phenylenediamine; 2-isopropyl-p-phenylenediamine; N-(2-hydroxypropyl)-p-phenylenediamine; 2-propyl-p-phenylenediamine; 1,3-N,N-bis-(2-hydroxyethyl)-N,N-bis (4-aminophenyl)-2-propanol; 2-methyl-4-dimethylaminoaniline; p-aminophenol; p-methylaminophenol; 3-methyl-p-aminophenol; 2-hydroxymethyl-p-aminophenol; 2-methyl-p-aminophenol; 2-(2-hydroxyethylaminomethyl)-p-aminophenol; 2-methoxymethyl-p-aminophenol; and 5-aminosalicylic acid; catechol; pyrogallol; o-aminophenol; 2,4-diaminophenol; 2,4,5-trihydroxytoluene; 1,2,4-trihydroxybenzene; 2-ethylamino-p-cresol; 2,3-dihydroxynaphthalene; 5-methyl-o-aminophenol; 6-methyl-o-aminophenol; and 2-amino-5-acetaminophenol; 2-methyl-1-naphthol; 1-acetoxy-2-methylnaphthalene; 1,7-dihydroxynaphthalene; resorcinol; 4-chlororesorcinol; 1-naphthol; 1,5-dihydroxynaphthalene; 2,7-dihydroxynaphthalene; 2-methylresorcinol; 1-hydroxy-6-aminonaphthalene-3-sulfonic acid; thymol (2-isopropyl-5-methylphenol); 1,5-dihydroxy-1,2,3,4-tetrahydronaphthalene; 2-chlororesorcinol; 2,3-dihydroxy-1,4-naphthoquinone; and 1-naphthol-4-sulfonic acid; m-phenylenediamine; 2-(2,4-diaminophenoxy)ethanol; N,N-bis(hydroxyethyl)-m-phenylenediamine; 2,6-diaminotoluene; N,N-bis(hydroxyethyl)-2,4-diaminophenetole; bis(2,4-diaminophenoxy)-1,3-propane; 1-hydroxyethyl-2,4-diaminobenzene; 2-amino-4 hydroxyethylaminoanisole; aminoethoxy-2,4-diaminobenzene; 2,4-diaminophenoxyacetic acid; 4,6-bis(hydroxyethoxy)-m-phenylenediamine; 2,4-diamino-5-methylphenetole; 2,4-diamino-5-hydroxyethoxytoluene; 2,4-dimethoxy 1,3-diaminobenzene; and 2,6-bis(hydroxyethylamino) toluene; m-aminophenol; 2-hydroxy-4-carbamoylmethylaminotoluene; m-carbamoylmethylaminophenol; 6-hydroxybenzomorpholine; 2-hydroxy-4-aminotoluene; 2-hydroxy-4-hydroxyethylaminotoluene; 4,6-dichloro-m-aminophenol; 2-methyl-m-aminophenol; 2-chloro-6-methyl-m-aminophenol; 2-hydroxyethoxy-5-aminophenol; 2-chloro-5-trifluoroethylaminophenol; 4-chloro-6-methyl-m-aminophenol; N-cyclopentyl-3-aminophenol; N-hydroxyethyl-4-methoxy-2-methyl-m-aminophenol and 5-amino-4-methoxy-2-methylpheno; 2-dimethylamino-5-aminopyridine; 2,4,5,6-tetra-aminopyrimidine; 4,5-diamino-1-methylpyrazole; 1-phenyl-3-methyl-5-pyrazolone; 6-methoxy-8-aminoquinoline; 2,6-dihydroxy-4-methylpyridine; 5-hydroxy-1,4-benzodioxane; 3,4-methylenedioxyphenol; 4-hydroxyethylamino-1,2-methylenedioxybenzene; 2,6-dihydroxy-3,4-dimethylpyridine; 5-chloro-2,3-dihydroxypyridine; 3,5-diamino-2,6-dimethoxypyridine; 2-hydroxyethylamino-6-methoxy-3-aminopyridine; 3,4-methylenedioxyaniline; 2,6-bis-hydroxyethoxy-3,5-diaminopyridine; 4-hydroxyindole; 3-amino-5-hydroxy-2,6-dimethoxypyridine; 5,6-dihydroxyindole; 7-hydroxyindole; 5-hydroxyindole; 2-bromo-4,5-methylenedioxyphenol; 6-hydroxyindole; 3-amino-2-methylamino-6-methoxypyridine; 2-amino-3-hydroxypyridine; 2,6-diaminopyridine; 5-(3,5-diamino-2-pyridyloxy)-1,3-dihydroxypentane; 3-(3,5-diamino-2-pyridyloxy)-2-hydroxypropanol and 4-hydroxy-2,5,6-triaminopyrimidine, or combinations thereof.

Conditioning Agents

As described above at least one of part ai and part aii of the compositions of the invention has about 0.01 to about 5.0% of a conditioning agent;

The conditioning compositions of this invention contain at least one water-soluble or water-dispersible quaternary nitrogen-containing conditioning agent that is also sometimes referred to herein as a cationic compound. A tertiary amidoamine may be additionally present in preferred compositions of the invention.

The quaternary nitrogen-containing conditioning agents are preferably present at from about 0.5 to about 5 percent by weight of the composition as an active ingredient. More preferably, the quaternary nitrogen-containing conditioning agent is present at from about 2 to about 3 weight percent, as an active ingredient.

The class of quaternary nitrogen-containing conditioning agents useful herein can contain one quaternary nitrogen atom having (a) two long aliphatic chains and (b) two identical or different short chain alkyl groups having one or two carbon atoms, each bonded to the quaternary nitrogen atom. The two long chains each can contain about 12 to about 18 carbon atoms.

Illustrative conditioning agents include distearyldimethylammonium chloride and dilauryidimethylammonium chloride. These compounds are named Quaternium-5 and Quaternium-47, respectively, in the CTFA Cosmetic Ingredient Dictionary, 2nd ed., 1977, published by the Cosmetic, Toiletry and Fragrance Association, Inc., hereinafter referred to as the CTFA Dictionary.

It is noted that the long aliphatic chain of the beforementioned conditioning agents need not be solely or primarily of one chain length, i.e., the long chain need not be cetyl, myristyl, lauryl or stearyl. Rather, conditioning agents whose long aliphatic chain contains a mixture of lengths can be used. Such conditioning agents are conveniently prepared from naturally occurring materials, such as tallow, coconut oil, soya oil and the like, or from synthetically produced mixtures. Examples of useful conditioning agents having mixed aliphatic chain lengths include dimethyldi-(hydrogenated tallow)ammonium chloride and dialkyldimethylammonium chloride wherein each alkyl group is a saturated group consisting primarily of 16 carbon atoms. These quaternary nitrogen-containing conditioning agents are named Quaternium-18 and Quaternium-31, respectively, in the CTFA Dictionary.

The compositions of this invention can also be in the form of emulsions that contain additional amounts of hydrophilic and/or hydrophobic ingredients. Emulsions containing additional hydrophobic materials are preferred. It is preferred that those emulsions be stable to phase separation at a temperature of about 25 degrees C.; for a period of about 24 hours or longer after their preparation. The emulsions are more preferably stable to phase separation at temperatures normally found in commercial product storage and shipping for periods of one year or more.

Buffering Agents

The final coloring compositions of the present invention (that is after part ai and part aii have been mixed) have a preferred pH in the range of from about 7.5 to about 12, more preferably from about 8 to about 10. Buffering agents may be used to achieve the desired pH ranges.

Buffering agents may be present in part ai compositions of the present invention. Hair coloring compositions of the present invention may also contain one or more hair swelling agents (HSAs) such as urea, to adjust the pH to the desired level. Several different pH modifiers can be used to adjust the pH of the final composition or any constituent part thereof.

Further examples of suitable buffering agents are ammonium hydroxide, ethylamine, dipropylamine, triethylamine and alkanediamines such as 1,3-diaminopropane, anhydrous alkaline alkanolamines such as, mono or di-ethanolamine, preferably those which are completely substituted on the amine group such as dimethylaminoethanol, polyalkylene polyamines such as diethylenetriamine or a heterocyclic amine such as morpholine as well as the hydroxides of alkali metals, such as sodium and potassium hydroxide, hydroxides of alkali earth metals, such as magnesium and calcium hydroxide, basic amino acids such as L-arginine, lysine, oxylysine and histidine and alkanolamines such as dimethylaminoethanol and aminoalkylpropanediol and mixtures thereof. Also suitable for use herein are compounds that form $HCO_3$—by dissociation in water (hereinafter referred to as 'ion forming compounds'). Examples of suitable ion forming compounds are $Na_2CO_3$, $NaHCO_3$, $K_2CO_3$, $(NH_4)_2CO_3$, $NH_4HCO_3$, $CaCO_3$ and $Ca(HCO_3)$ and mixtures thereof.

As herein before described certain alkaline buffering agents such as ammonium hydroxide and monoethylamine (MEA), urea and the like can also act as hair swelling agents (HSA's) such as urea and the like.

The permanent hair coloring compositions of the present invent can come in hair coloring packages or kits.

Preferred for use as a buffering agent for the hair coloring compositions according to the present invention are ammonium hydroxide and/or sodium hydroxide.

In oxidizing and coloring kits comprising a portion of peroxide oxidizing agent, which may be present in either solid or liquid form, such as hydrogen peroxide, a buffering agent solution is required to stabilize hydrogen peroxide. Since hydrogen peroxide is stable in the pH range from 2 to 4, it is necessary to use a buffering agent having a pH within this range. Dilute acids are suitable hydrogen peroxide buffering agents. Phosphoric acid is a preferred agent for buffering hydrogen peroxide solutions.

This pH adjustment also can be effected by using well known acidifying agents in the field of treating keratinous fibers, and in particular human hair, such as inorganic and organic acids such as hydrochloric acid, tartaric acid, citric acid, and carboxylic or sulphonic acids such as ascorbic acid, acetic acid, lactic acid, sulphuric acid, formic acid, ammonium sulphate and sodium dihydrogenphosphate/phosphoric acid, disodium hydrogen phosphate/phosphoric acid, potassium chloride/hydrochloric acid, potassium dihydrogen phthalate/hydrochloric acid, sodium citrate/hydrochloric acid, potassium dihydrogen citrate/hydrochloric acid, potassium dihydrogencitrate/citric acid, sodium citrate/citric acid, sodium tartarate/tartaric acid, sodium lactate/lactic acid, sodium acetate/acetic acid, disodium hydrogenphosphate/citric acid and sodium chloride/glycine/hydrochloric acid and mixtures thereof.

Shampoing Agents or Cleansing Agents or Surfactants

The compositions of the present invention can additionally contain a surfactant system. Suitable surfactants for inclusion in the compositions of the invention generally have a lipophilic chain length of from about 8 to about 22 carbon atoms. Surfactants which are either amphoteric or anionic or zwitterionic are included in compositions of the present invention which have a shampoo base. In addition, there may be included in shampoo compositions of the present invention, cationic, nonionic or zwitterionic surfactants. Compositions of the invention have a shampoo base which can include cationic, nonionic or zwitterionic surfactants. Surfactants may be present in part ai and part aii compositions of the invention.

(i) Anionic Surfactants

Anionic surfactants suitable for inclusion in the compositions of the invention include alkyl sulphates, ethoxylated alkylsulphates, alkyl glyceryl ether sulfonates, methyl acyl taurates, fatty acyl glycinates, N-acyl glutamates, acylisethionates, alkyl sulfosuccinates, alkyl ethoxysulphosuccinates, alpha-sulfonated fatty acids, their salts and/or their esters, alkyl ethoxy carboxylates, alkyl phosphate esters, ethoxylated alkyl phosphate esters, alkyl sulphates, acylsarcosinates and fatty acid/protein condensates, and mixtures thereof. Alkyl and/or acyl chain lengths for these surfactants are C12–C22, preferably C12–C18 more preferably C12–C14.

(ii) Nonionic Surfactants

The compositions of the invention can also comprise water-soluble nonionic surfactants.

Suitable oil derived nonionic surfactants for use herein include water soluble vegetable and animal-derived emollients such as triglycerides with a polyethyleneglycol chain inserted; ethoxylated mono and di-glycerides, polyethoxylated lanolins and ethoxylated butter derivatives.

Preferred for use herein are polyethyleneglycol based polyethoxylated $C_9$–$C_{15}$ fatty alcohol nonionic surfactants containing an average of from about 5 to about 50 ethyleneoxy moieties per mole of surfactant.

Also suitable for use herein are nonionic surfactants derived from composite vegetable fats extracted from the fruit of the Shea Tree (Butyrospermum Karkii Kotschy) and derivatives thereof. Similarly, ethoxylated derivatives of Mango, Cocoa and Illipe butter may be used in compositions according to the invention. Although these are classified as ethoxylated nonionic surfactants it is understood that a certain proportion may remain as non-ethoxylated vegetable oil or fat.

Other suitable oil-derived nonionic surfactants include ethoxylated derivatives of almond oil, peanut oil, rice bran oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, and sunflower seed oil.

(iii) Amphoteric Surfactants

Amphoteric surfactants suitable for use in the compositions of the invention include: alkyl betaines, alkyl sultaines, alkyl amphoacetates, alkyl amphodiacetates, alkyl amphopropionates, and alkyl amphodipropionates.

(iv) Zwitterionic Surfactants

Water-soluble auxiliary zwitterionic surfactants suitable for inclusion in the compositions of the present invention include alkyl betaines Water-soluble auxiliary sultaine surfactants suitable for inclusion in the compositions of the present invention include alkyl sultaines. Preferred for use herein is coco amido propylhydroxy sultaine.

Water-soluble auxiliary amine oxide surfactants suitable for inclusion in the compositions of the present invention include alkyl amines and amido amine oxides number. Preferred amine oxides include cocoamidopropylamine oxide, lauryl dimethyl amine oxide and myristyl dimethyl amine oxide.

(v) Cationic Surfactants

Cationic surfactants include polyethylene condensates of alkyl phenols, condensation products of ethylene oxide, propylene oxide, and ethylene oxide, propylene oxide, and ethylene diamine, long chain tertiary amine oxides, long chain tertiary phosphine oxides, and the like.

Solvents

Water is the preferred principal diluent for the compositions according to the present invention. As such, the compositions according to the present invention may include one or more solvents as additional diluent materials. Generally, the solvent is selected to be miscible with water and innocuous to the skin. Solvents suitable for use herein include $C_1-C_{20}$ mono- or polyhydric alcohols and their ethers, glycerine, with monohydric and dihydric alcohols and their ethers preferred. In these compounds, alcoholic residues containing 2 to 10 carbon atoms are preferred. Thus, a particularly preferred group includes ethanol, isopropanol, n-propanol, butanol, propylene glycol, ethylene glycol monoethyl ether, and mixtures thereof.

These solvents may be present in compositions of the present invention. These solvents may be present in part ai compositions of the invention and part aii compositions of the invention.

Structuring Agents (Structurants) or Thickening Agents

Structuring agents or thickening agents may be included in compositions of the invention which have a shampoo base, and compositions of the invention which have a conditioner base, and thickeners may be included in part A and part B compositions of the invention. Long chain fatty alcohols having from about 11 to about 18 carbon atoms in the long fatty chain can be thickener constituents of the conditioning emulsions of this invention. These alcohols can be used alone, or in admixture with each other. When included in the compositions, the alcohol is preferably present at from about 0.5 to about 15 weight percent of the composition, and more preferably at from about 2 to about 10 weight percent.

Lauryl alcohol, oleyl alcohol, myristyl alcohol, stearyl alcohol, and the like, and mixtures thereof are contemplated herein. In addition, mixtures of natural or synthetic fatty alcohols having fatty chain lengths of from about 11 to about 18 carbons are also useful. Several such mixtures are available commercially, and are exemplified by the material containing a mixture of synthetic alcohols with 12 to 15 carbons in the alkyl chain sold under the trademark NEODOL 25 by Shell Chemical Company, and the material containing a mixture of synthetic alcohols with chain lengths of 12 to 16 carbons sold under the trademark ALFOL 1216 Alcohol by Conoco Chemicals.

Thickening agents suitable for use in the compositions herein may also be selected from oleic acid, cetyl alcohol, oleyl alcohol, sodium chloride, cetearyl alcohol, stearyl alcohol, synthetic thickeners such as Carbopol, Aculyn and Acrosyl and mixtures thereof. Preferred thickeners for use herein are Aculyn 22 (RTM), steareth-20 methacrylate copolymer; Aculyn 44 (RTM) polyurethane resin and Acusol 830 (RTM), acrylates copolymer that are available from Rohm and Haas, Philadelphia, Pa., USA. Additional thickening agents suitable for use herein include sodium alginate or gum arabic, or cellulose derivatives, such as methyl cellulose or the sodium salt of carboxymethylcellulose or acrylic polymers.

Fatty alcohols of the above discussed carbon chain lengths which are ethoxylated to contain an average of one or two moles of ethylene oxide per mole of fatty alcohol can be used in place of the fatty alcohols themselves. Examples of such useful ethoxylated fatty acids include ethylene glycol cetyl ether, polyoxyethylene (2) stearyl ether, and the like; the exemplary compounds having CTFA Dictionary names of Ceteth-1 and Steareth-2, respectively.

Optional Ingredients

The compositions of the present invention can comprise a wide range of optional ingredients. Examples of these functional classes include: anticaking agents, antioxidants, binders, biological additives, bulking agents, chelating agents, chemical additives, colorants, cosmetic astringents, cosmetic biocides, denaturants, drug astringents, emulsifiers, film formers, fragrance components, humectants, opacifying agents, plasticizers, preservatives, propellants, reducing agents, solvents, foam boosters, hydrotropes, solubilizing agents, suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include solubilizing agents, sequestrants, and the like.

Other optional ingredients include organic acids. A non-exclusive list of examples of organic acids which can be used as the proton donating agent are adipic acid, tartaric acid, citric acid, maleic acid, malic acid, succinic acid, glycolic acid, glutaric acid, benzoic acid, malonic acid, salicylic acid, gluconic acid, polyacrylic acid, their salts, and mixtures thereof. Non-exclusive lists of examples of mineral acid for use herein are hydrochloric, phosphoric, sulfuric and mixtures thereof.

It has been found by experimentation that daily hair care products can achieve permanent or durable desired hair color. As noted above, the daily hair care product consists of two parts.

part ai: oxidative hair dyes in a shampoo base at alkaline pH; and wherein part ai optionally has about 0.01 to about 5.0% of a conditioning agent, and optionally has about 0.01 to about 10.0% of a structurant;

part aii: an oxidative compound in a shampoo base at acidic pH and wherein part aii optionally has about 0.01 to about 5.0% of a conditioning agent; and optionally has about 0.01 to about 10.0% of a structurant;

part ai is mixed with part aii and applied to hair. The reason conventional hair coloring products come in two packages is because the mixture of the coloring component and the oxidizing component is unstable and the two components must be kept apart until just before use. Similarly part ai and part aii of the present invention must be kept apart until just before use. By varying the concentration of the actives and the treatment time, the amount of color on hair can be varied while minimizing hair damage. To make the product more convenient and fool proof, part ai and aii can be packaged in dual dispensing systems where both parts are mixed outside of the package, when dispensed. It is understood that at least one of part aii and part aii as described above has about 0.01 to about 5.0% of a conditioning agent. Part ai and part aii can be mixed in about a 1.2:0.8 to about 0.8:1.2 ratio, respectively, more preferably about a 1:1 ratio.

The mixture is then applied to wet hair. Depending upon the amount of color desired, the treatment time could be varied from about 10 seconds to about two minutes or longer.

Such shampooing treatments would add color to hair gradually without damage due, for example, to lower contact time. Each subsequent treatment would add color until the desired shade is obtained. Depending upon the concentration of the actives and contact time, a desired shade may be reached in six to eight treatments. It has been found that since any one treatment does not exceed the threshold of irreversible damage, the total damage resulting from multiple treatments is lower than the damage from a single conventional treatment. Such a process gives the user control over the amount of color deposited on his or her hair, and also the option to discontinue further applications if the color first delivered is not to his or her liking. She or he also has the option to switch to another color shade immediately without having to wait the six to eight weeks that is recommended for conventional treatments. With conventional hair color treatment, it is not recommended to perm and color hair simultaneously due to extensive damage. However, since this method of the present invention colors the hair with minimum damage, perming can be done in the same time frame. Moreover, the presence of conditioner in either part ai or part aii or both, causes hair that is being colored to be conditioned at the same time. This gives the hair good feel and manageability for example.

Thus, if the contact time is kept at about two minutes or below for each treatment with compositions of the invention then there is no appreciable hair damage no matter how many hair color application treatments, according to the methods of the invention are preformed.

At the same time that hair damage is avoided by the methods of the invention, the consumer's hair is gradually being brought to the desired shade and color. This gradual change of color has two advantages: first, since the color is changed gradually, the consumer can stop the process if he or she does not like the color his or her hair is turning to. Second, some consumers do not want an abrupt change in color because they may feel embarrassed in public after having made such an abrupt change to the color of their hair. Moreover, the method and compositions of the present invention can be used in the shower, and on a daily basis, because the compositions and methods of the present invention, by contrast with conventional color compositions, do not employ poisonous levels of chemicals and also because compositions methods of the present invention involve hair application steps that are often up to only about two minutes in length. By contrast conventional hair coloring compositions require approximately 30 minutes' time for each application, an amount of time, which is clearly not suitable for use in the shower.

Also compositions of the present invention can have a shampoo base, and therefore the compositions of the present invention, cleanse the hair and remove debris from the hair. Compositions of the present invention can be used on a daily basis, in the shower or bath, for example, as part of a daily hair care cleansing regimen. Compositions of the present invention, as noted above, add gradual permanent color to the hair, minimize hair root outgrowth, and help to prevent hair color fading.

The methods of the present invention are not as messy as conventional permanent hair coloring methods. The methods of the present invention do not use chemical compositions that are smelly and noxious such as those used in conventional permanent hair-coloring methods. Because the methods of the invention can be carried out in the shower, they do not involve the dripping and the mess associated with conventional permanent hair coloring which is done outside of the shower. The methods of the present invention do not use chemical compositions that can stain fixtures in the bathroom or that will stain the scalp and the face.

Compositions part ai and part aii upon mixture, form a composition with a pleasing viscosity and that is pleasing to the fingers. This is because the compositions part ai and part aii contain a shampoo agent.

A dual package or kit can be used to contain separately, the compositions, part ai and part aii of the present invention. A dual package which can be employed in the products and kits of the present invention is U.S. Pat. No. 6,082,588 to Markey et al which is hereby incorporated by reference.

Kit Containing an Instruction Sheet

As noted just above, the invention also relates to a package or kit for carrying out the permanent hair coloring methods of the present invention. The kit can comprise a developer solution, a hair coloring or dye solution and a post treatment solution, each in a separate container or in a dual container, as described herein. The kit can also contain written instructions that explain how the compositions of the invention are used.

The consumer admixes the components of the kit according to written instructions, to obtain the aqueous reaction mixture. The admixture may be carried out in a separate vessel external to the kit, or may take place in a container of the kit, adapted to provide sufficient head space for mixing. The components that are mixed are the developer composition and the hair colorant or dye composition. The components or reactants may also be admixed on the hair of the user. Essentially upon mixing, reaction of the hair colorant or dye and the developer will commence. After treatment for a desired time, the mixture of hair developer and hair dye may be removed, preferably with water or a conventional shampoo or a conventional conditioning shampoo. Since the contact times of the compositions or mixtures of the present invention, are relatively short as described herein, the hair may be contacted with the compositions or mixtures of the invention, while the consumer is in the shower as part of his or her daily hair cleansing regimen, for example.

As noted above, hair colorant or dye composition and peroxygen or developer composition are mixed together, and the resulting mixture may be applied to the hair and allowed to remain for a set time, usually about one half minute to about 2 minutes or about one half minute to about one and a half minutes.

Desired change in permanent hair color by methods of the invention are described by the mathematical formulas described herein. The monitoring of desired change in hair color can be achieved in a number of ways. In the first instance, the consumer can compare his or her hair color with the hair color of a sample tress. Hair dyeing by the method of the invention can be repeated until her hair color matches the desired hair color. It is noted that the compositions used in the methods of the invention have lower contact times and thus repeated use of these compositions will not cause hair damage. An unexpected discovery of the present invention is that for damage to hair to occur, contact time in each treatment must go above the threshold value of about two minutes. Thus, the consumer can lighten or color the hair through repeated applications wherein the duration of each color application is about two minutes or less. The following two advantages are thereby achieved: first, there is a stepwise approach to the desired color; and second, a minimum of hair damage is done.

By the methods of the present invention, permanent durable desired hair color, with longer lasting hair, clean soft feel, and a minimum of hair damage is achieved.

Desired hair color can also be reached by comparing hair after each treatment until it matches hair tresses taken from the consumer during a prior hair coloring treatment.

Desired hair color can also be reached by testing the hair after each treatment with instruments, which measure the color of the hair. When the measurements of hair color of the treated hair reach a desired level, the treatment can be stopped.

The consumer also can compare the color of his or her hair with the desired hair color, which can be printed on the package of the product. The consumer can also vary the number of days of application of the product, and the consumer can also vary the amount of time the mixture of part ai and part aii is left in the hair on each application. The number of applications can vary from about 7 to about 30 applications, or the number of applications can be continued indefinitely, so as to maintain fresh hair color for an indefinite amount of time. The time of each application can vary from, for example, about 1 to about two minutes.

The monitoring of hair color change, until the desired hair color is reached or so as to insure that the desired hair color is maintained, can be done in fact by the use of any matching or comparison method commonly employed in the art.

The method of the invention occurs over the course of days. Therefore, the final color of the consumer's hair may be affected by the amount of exposure to the sun of the hair during the course of treatment.

The following examples were made by mixing the below listed ingredients. The following examples, which were made, are shown as illustrations only and are not intended to limit the scope of the invention:

EXAMPLE #1

| Formula #1 | |
|---|---|
| Dark Brown Color shampoo: Part ai | |
| DI (deionized)Water | 27.56 |
| Sodium metabisulfite | 0.15 |
| M-amino phenol | 0.03 |
| O-amino penol | 0.05 |
| Rodol gray HED | 0.13 |
| p-Phenylenediamine | 0.70 |
| Resorcinol | 0.35 |
| Cocaamidopropyl betaine | 4.50 |
| Carbopol 980 | 0.3 |
| Cocamide MEA | 2.5 |
| Sodium C14–C16 olefin sulfonate | 45.00 |
| Lauryl alcohol | 10.0 |
| Sodium dihydrogen phosphate | 0.20 |
| Ethylene glycol distearate | 0.50 |
| Dimethiconol and TEA-dodecylbenzenesulfate | 3.2 |
| Silicone microemulsion | 1.0 |
| Sodium chloride | 1.6 |
| Propylene glycol | 0.3 |
| Versene | 0.2 |
| Fragrance | 0.2 |
| Kathon CG | 0.08 |
| DMDM Hydantoin | 0.1 |
| Sodium hydroxide 50% | 0.85 |
| PH = 8 to 9 | |
| Dark Brown Color shampoo: Part aii | |
| D.I. Water | 21.00 |
| Jaguar Excell | 0.10 |
| Lauramine oxide | 3.7 |
| Sodium C14–C16 olefin sulfonate | 45.00 |
| Sodium dihydrogen phosphate | 0.20 |
| Lauryl alcohol | 5.0 |
| Silicone microemulsion, DC2-1870 HV | 5.12 |
| Silicone microemulsion SME 253 | 1.0 |
| Phosphoric acid, 85% | 0.09 |
| DMDM Hydantoin 55% | 0.10 |

-continued

| Formula #1 | |
|---|---|
| Fragrance | 0.20 |
| Sodium chloride | 2.2 |
| Hydrogen Peroxide(35%) | 10.00 |
| PH = 3.0 | |

Wet the hair tresses. Take equal amounts of color shampoo of part ai and aii (formula#1), mix and apply to the wet hair tresses, wait for one minute, and rinse well. Repeat the above procedure for subsequent treatments. Collect the hair tress after 2, 5 8, 11 and 15 treatments. Measure the change in color delta E using McBeth Coloreye.

EXAMPLE #2

L'Oreal Dark Brown permanent hair color

Color the hair tresses using L'Oreal dark brown permanent hair color. Follow the instruction sheet. Measure the change in color delta E using McBeth coloreye.

The changes in delta E values are summarized in the below table. It can be seen from the results that changes in hair color after one 30-minute treatment with L'Oreal Dark Brown (which is a conventional hair coloring treatment) is very similar to fifteen 1-minute treatments of a hair coloring composition of the present invention. Again, It took about 15 treatments with compositions of the invention to achieve a color change similar to a single 30 minutes' conventional permanent hair coloring treatment.

| | L'Oreal's Preference: Dark Brown: Delta E | Dark Brown shampoo Delta E |
|---|---|---|
| 1X-30 min. | 47.36 | |
| 2X-1 min. | | 14.235 |
| 5X-1 min. | | 23.478 |
| 8X-1 min. | | 30.243 |
| 11X- min | | 37.45 |
| 13X- 1 min | | 42.167 |
| 15X-1 min | | 48.765 |

Yield Stress or Flow Property to Assess Dripping Problem

Most of the shampoos have very little yield stress means it requires little energy to flow. Since conventional shampoos have very low yield stress, which can give dripping problems. To reduce the dripping problem, we need to formulate the shampoo with higher yield stress index. The higher the yield stress index indicates better flowing product. Generally, higher than 1000-yield stress index gives good non dripping product The yield stress index = yield stress force of the invented composition/ yield stress force of conventional Shampoo (e.g. THERMASILK moisturizing shampoo)

= 12 Pascal force/0.01 Pascal force

= 1200

Thus, if the contact time is kept at about two minutes or below for each treatment with compositions of the invention then there is no hair damage no matter how many hair color application treatments are performed according to the methods of the invention.

Treatment of hair with compositions of the invention as described herein gives said hair good attributes such as lower amounts of cysteic acid (which are an indicator of hair damage), good hair color change, less color fading, less damage to hair, and more intense color to hair as described just below. Also described below is a method for applying composition of the invention at set time intervals so as to avoid root outgrowth.

The following mathematical formulas describe the color change results and the hair damage results, which are obtained through the use of the compositions and methods of the present invention.

Assessment of Damage
Combing index—

A combing experiment has been carried out to evaluate the extent of hair damage caused by the application of hair coloring compositions. Wet combing evaluation techniques have been used to evaluate resulting hair damage. A higher index number (more than one) indicates lower damage.

Combing index=Combing force of untreated hair/combing force of treated with color shampoo The above tresses were evaluated via Instron to measure combing force.

| Treatments | Combing force(gmforce) |
|---|---|
| Untreated Hair | 26.15 |
| Treated with Color Shampoo | 17.27 |

$$\text{Combing index} = \text{Combing force of untreated hair}/$$
$$\text{combing force of treated with color shampoo}$$
$$= 26.15/17.27$$
$$= 1.51$$

Wet Combing Force:

After conventional hair color treatment, it is hard to comb the hair. The greater the difficulty there is in combing the hair the more hair damage has occurred. The combing force was measured using an Instron instrument. The combing force that results from treatment of hair with compositions of the invention can range from about 5 to about 55 gmforce, preferably about 5 to about 20 and more preferably about 5 to about 10 gmforce.

The combing force composition that results from treatment of hair with compositions of the invention can range from about 5 to about 55; or about 10 to about 55 gmforce, preferably about 12 to about 30 and more preferably about 10 to about 20 gmforce.

Break Stress:

After conventional hair color treatment, the hair becomes weak and easy to break. The weak hair is again a sign of damage. The strength of the hair was measured using Instron.

The break stress with composition would be in the range of 0.005 to 0.03 gmforce/micron, preferably 0.005 to 0.025 and more preferably 0.005 to 0.018 gmforce/micron.

Cysteic Acid:

Much of the hair damage associated with conventional hair color treatment comes from the oxidation of cystine residues to the corresponding cysteic acid, with a consequent decrease in the tensile strength of hair as these cross-linkages are destroyed. A good measure of oxidative damage is thus the amount of cysteic acid formed in hair.

Infrared transmission spectroscopy has been used to determine cysteic acid content in hair. The ratio of absorption at 1040 cm-1/absorption at 1240 cm-1 (1040/1240 ratio) would indicate the extent of damage. Lower the ratio indicates less hair damage.

The ratio of 1040/1240 resulting from use of a composition of the invention composition would be in the range of about 0.01 to about 1.5, preferably about 0.01 to about 1.0, and more preferably about 0.01 to about 0.4.

Total Hair Damage:

Hair damage done by hair coloring compositions can be calculated according to the following mathematical formulas:

% Damage=Chemical damage×Physical damage

% Damage=amount of cysteic acid×combing forcegm×breaking stress forcegm/micron2×100

% Damage using L'Oreal's conventional preference permanent hair color for example=0.75×48×0.02×100=72% damage % Damage using new hair color composition:0.25×20×0.015× 100=7.5% damage The above numbers indicate that the hair color compositions and methods of the invention damage hair much less than conventional permanent hair color treatment.

Color Change/Color Control:

A conventional permanent hair color system gives a color change delta E of about 5 to about 65 on blonde hair, and color change of delta E of about 1 to about 8 on brown hair with one treatment. In conventional hair coloring treatments, consumers have little or no control of color, control of hue and control of lightening.

With the present composition and methods, there can be can delivered delta E of about 0.1 to about 65 on blonde hair and delta E of about 0.1 to about 8 on brown hair.

Root Outgrowth:

Conventional permanent hair color systems are used once every 4 to 6 weeks. During this time because of new hair growth, roots look totally different than rest of the hair. On average hair grows 1 cm/month or 0.3 mm/day.

With the present compositions and methods, one would add color on each application of said compositions. Laboratory evaluation indicates that one would add 7% color change for each shampooing treatment.

The amount of color added is determined by the following mathematical formulas.

$$\text{The length of the new hair} = 0.3 \text{ mm} \times \text{no. of days}$$
$$\% \text{ color added to new hair (in 14 days)} = \text{No of days} \times$$
$$\% \text{ color added per day}$$
$$= 14 \times 7\%$$
$$= 98\% \text{ color}$$

Due to the constant addition of the color change of 7% per day, one will not be able to see root outgrowth during treatment using compositions and methods of the present invention.

Color Fading:

Conventional permanent hair color systems are used about once every 4 to 6 weeks. During this time color fades with washing, and outside exposure, due to the weathering effect. The amount of color fading will depend upon the frequency of washing and the amount of outside exposure. Assuming that a person washes his/her hair 4 times a week and is outdoors for 2.0 hrs a day, the percentage of the color loss can be calculated using following equation.

Laboratory evaluation indicates that one would loose 1% of the color per wash and would lose about 0.75% of the color/hr of outside exposure $$\% \text{ Loss of color} = \text{no. of washings} \times \% \text{ color loss/wash} +$$
$$\text{no of hrs. of exposure} \times \% \text{ color loss/hr}$$
$$\% \text{ Loss of color per month} = 20 \times 1.0 + 40 \text{ hrs} \times 0.75$$
$$= 20 + 30$$
$$= 50\%$$
$$\% \text{ Loss of color per week} = 12.5\%$$

So, an average consumer would loose 50% of hair color per month. That is why most consumers want to recolor their hair every 4 to 6 weeks.

With the present composition and methods, one would add color on each application of composition, according to the schedule set forth by the following mathematical formulas.

$$\% \text{ Color addition/week} = \text{no of shampoo treatment week} \times \text{amount color added/treatment}$$

Laboratory evaluation indicates that one would add 7% of color change per shampoo treatment.

$$\% \text{ Color addition/week} = 3 \times 7\% = 21\%$$

With the present compositions, one would lose 12.5% of the color per day but would add 21% of the color per day. Due to this, one would not see any fading of the color and color stays fresh everyday.

More Intense Color:

The typical permanent color composition, upon application goes through an oxidation mechanism. Each of the dye intermediates can produce pigments through oxidation and polymerization. According to Le Chatelier's principle, the state of a chemical reaction is a dynamic state in which the chemical reaction is occurring in both directions. The rate of the reaction depends upon the ratio of the rate of the forward reaction to the rate of the backward reaction. The higher the ratio the faster is the reaction. The factors affecting the rate of reactions are as follows:

1. Reactants
2. Products
3. Pressure; and
4. Temperature

A main difference in the reaction using conventional permanent hair color systems and new invented system is the temperature at which the treatment is carried out. With the conventional system, the reaction takes place at room temperature, at about 70–75° F., while with the methods of the present invention, since they can be carried out in the shower, the reaction takes place at higher temperatures of about 100 to 110° F. According to le Chatelier's principle, the effect of temperature is very significant to the final rate of reaction.

Under identical conditions, laboratory evaluation indicates that one would increase 5% intensity of the color with 10° F.-temperature difference.

Therefore, according to the mathematical formula just below, 15% more color is added using the compositions and methods of the invention as opposed to conventional hair coloring methods.

$$\% \text{ Additional Color} = \text{delta } T \times \% \text{ change in color per one degree F. difference}$$
$$= (100 \text{ F.} - 70 \text{ F.}) \times 0.5$$
$$= 30 \times 0.5 = 15\% \text{ more color due to new method}$$

The following additional compositions of the invention were also made:

EXAMPLE 3

| | Hair Coloring Shampoo: (Part-ai) | | | | Hair Coloring Shampoo: Set#3(Part-A) | | |
|---|---|---|---|---|---|---|---|
| Ingredients | Dark Brown | Light Brown | Dark Blonde | Light Blonde | Dark Auburn | Medium Auburn | Light Auburn |
| Deionized water | 60.00 | 60.00 | 60.00 | 60.00 | 60.00 | 60.00 | 60.00 |
| Polymer JR | 0.30 | 0.30 | 0.30 | 0.30 | 0.30 | 0.30 | 0.30 |
| Cocamidopropyl betaine | 7.00 | 7.00 | 7.00 | 7.00 | 7.00 | 7.00 | 7.00 |
| SCAP | 25.00 | 25.00 | 25.00 | 25.00 | 25.00 | 25.00 | 25.00 |
| DC-1870 HV | 1.60 | 1.60 | 1.60 | 1.60 | 1.60 | 0.08 | 1.60 |
| Propylene glycol | 0.30 | 0.30 | 0.30 | 0.30 | 0.30 | 0.30 | 0.30 |
| Lauryl alcohol | 10.00 | 10.00 | 10.00 | 10.00 | 10.00 | 10.00 | 10.00 |
| Sodium phosphate | — | 0.20 | 0.20 | 0.20 | 0.20 | 0.20 | 0.20 |
| Versene 100 | 0.20 | 0.20 | 0.20 | 0.20 | 0.20 | 0.20 | 0.20 |
| Fragrance | 0.20 | 0.20 | 0.20 | 0.20 | 0.20 | 0.20 | 0.20 |
| Kathon CG(1.5% active) | 0.08 | 0.08 | 0.08 | 0.08 | 0.08 | 0.08 | 0.08 |
| DMDM hydantoin | 0.10 | 0.10 | 0.10 | 0.10 | 0.10 | 0.10 | 0.10 |
| Sodium metabisulfite | 0.15 | 0.15 | 0.15 | 0.15 | 0.15 | 0.15 | 0.15 |
| 4-amino-2-hydroxytoluene(p-amino-o-cresol)PAOC | — | — | — | — | 0.70 | 0.30 | 0.70 |
| m-aminophenol: Rodol EG | 0.03 | — | — | — | — | — | — |
| o-aminophenol: Rodol 2G | 0.05 | 0.01 | 0.05 | 0.03 | 0.20 | 0.15 | 0.10 |
| p-aminophenol: Rodol P base | — | — | 0.05 | 0.03 | 0.20 | 0.15 | 0.30 |
| N,N Bis(2-hydroxyethyl)-p-phenylenediamine sulfate: HED | 0.13 | — | — | — | — | — | — |

-continued

| | | | | | | | |
|---|---|---|---|---|---|---|---|
| 2-methylresorcinol: RodolMRP | — | — | — | — | — | — | — |
| 1-Napthol: Rodol ERN | — | — | — | — | — | — | — |
| p-phenylenediamine: Rodol D type J | 0.70 | 0.35 | 0.02 | 0.01 | 0.15 | 0.10 | 0.03 |
| Resorcinol: Rodol RS | 0.35 | 0.45 | 0.03 | 0.01 | 0.03 | 0.05 | 0.03 |
| Phenyl methyl pyrozolone(Rodol PMP | — | 0.01 | — | — | — | — | — |
| HC Red#3 | — | — | — | 0.20 | 0.15 | 0.02 | |
| Sodium hydroxide, liquid 50% active | 0.4–0.6 | 0.4–0.6 | 0.4–0.6 | 0.4–0.6 | 0.4–0.6 | 0.40 | 0.4–0.6 |
| Mixed pH = | 7.5–8.0 | 9.0–9.5 | 9.0–9.5 | 9.0–9.5 | 8.0–8.5 | | 9.0–9.5 |

Hair Coloring Shampoo: Part aii(Peroxide phase)

| Chemical Name | Actual Weight % | Actual Weight % |
|---|---|---|
| D.I. Water | 39.00 | 29.00 |
| Polymer JR 30M | 0.30 | 0.30 |
| Sodium C14–C16 Olefin Sulfonate | 35.00 | 35.00 |
| Lauramine oxide 29% | 3.70 | 3.70 |
| Lauryl alcohol | 5.00 | 5.00 |
| DC-1870 HV | 1.60 | 1.60 |
| DI water | 9.00 | 9.00 |
| DMDM Hydantoin 55% | 0.10 | 0.10 |
| Hydrogen peroxide, 35% | 10.00 | 20.00 |
| Fragrance | 0.20 | 0.20 |
| Phosphoric acid, 85% | 0.60 | 0.60 |

Specification:
pH = 2.7 to 3.0
Viscosity = 3000 to 6000 cps(spindle#4, 20 rpm)

EXAMPLE 4

Hair Coloring Shampoo (Part-ai)

| Ingredients | Dark Brown | Light Brown | Dark Blonde | Light Blonde | Dark Auburn | Medium Auburn | Light Auburn |
|---|---|---|---|---|---|---|---|
| Deionized water | 40.00 | 40.00 | 40.00 | 40.00 | 40.00 | 40.00 | 40.00 |
| Carbopol-980 | 0.30 | 0.30 | 0.30 | 0.30 | 0.30 | 0.30 | 0.30 |
| Cocamidopropyl betaine | 4.50 | 4.50 | 4.50 | 4.50 | 4.50 | 4.50 | 4.50 |
| Cocamide MEA | 2.50 | 2.50 | 2.50 | 2.50 | 2.50 | 2.50 | 2.50 |
| Sodium C14–C16 Olefin sulfonate | 45.00 | 45.00 | 45.00 | 45.00 | 45.00 | 45.00 | 45.00 |
| Ethylene glycol distearate | 0.50 | 0.50 | 0.50 | 0.50 | 0.50 | 0.50 | 0.50 |
| Propylene glycol | 0.30 | 0.30 | 0.30 | 0.30 | 0.30 | 0.30 | 0.30 |
| Lauryl alcohol | 10.00 | 10.00 | 10.00 | 10.00 | 10.00 | 10.00 | 10.00 |
| Sodium phosphate | 0.20 | 0.20 | 0.20 | 0.20 | 0.20 | 0.20 | 0.20 |
| Dimethiconol and TEA-dodecylbenzenesulfate | 3.20 | 3.20 | 3.20 | 3.20 | 3.20 | 3.20 | 3.20 |
| Silicone microemulsion | 1.00 | 1.00 | 1.00 | 1.00 | 1.00 | 1.00 | 1.00 |
| Versene 100 | 0.20 | 0.20 | 0.20 | 0.20 | 0.20 | 0.20 | 0.20 |
| Fragrance | 0.20 | 0.20 | 0.20 | 0.20 | 0.20 | 0.20 | 0.20 |
| Kathon CG(1.5% active) | 0.08 | 0.08 | 0.08 | 0.08 | 0.08 | 0.08 | 0.08 |
| DMDM hydantoin | 0.10 | 0.10 | 0.10 | 0.10 | 0.10 | 0.10 | 0.10 |
| Sodium metabisulfite | 0.15 | 0.15 | 0.15 | 0.15 | 0.15 | 0.15 | 0.15 |
| 4-amino-2-hydroxytoluene (p-amino-o-cresol)PAOC | — | — | — | — | 0.70 | 0.30 | 0.70 |
| m-aminophenol: Rodol EG | 0.03 | — | — | — | — | — | — |

-continued

| | | | | | | | |
|---|---|---|---|---|---|---|---|
| o-aminophenol: Rodol 2G | 0.05 | 0.01 | 0.05 | 0.03 | 0.20 | 0.15 | 0.10 |
| p-aminophenol: Rodol P base | — | — | 0.05 | 0.03 | 0.20 | 0.15 | 0.30 |
| N,N Bis(2-hydroxyethyl)-p-phenylene-diamine sulfate:HED | 0.13 | — | — | — | — | — | — |
| 2-methylresorcinol: RodolMRP | — | — | — | — | — | — | — |
| 1-Napthol:Rodol ERN | — | — | — | — | — | — | — |
| p-phenylenediamine: Rodol D type J | 0.70 | 0.35 | 0.02 | 0.01 | 0.15 | 0.10 | 0.03 |
| Resorcinol:Rodol RS | 0.35 | 0.45 | 0.03 | 0.01 | 0.03 | 0.05 | 0.03 |
| Phenyl methyl pyrozolone(Rodol PMP | — | 0.01 | — | — | — | — | — |
| HC Red#3 | — | — | — | — | 0.20 | 0.15 | 0.02 |
| Sodium hydroxide, liquid 50% active | 0.4–0.6 | 0.4–0.6 | 0.4–0.6 | 0.4–0.6 | 0.4–0.6 | 0.40 | 0.4–0.6 |
| DI water | QS-100 | QS-100 | QS-100 | QS-100 | QS-100 | QS-100 | QS-100 |
| Mixed pH = | 7.5–8.0 | 9.0–9.5 | 9.0–9.5 | 9.0–9.5 | 8.0–8.5 | | 9.0–9.5 |

Hair Coloring Shampoor:
Part aii (Peroxide phase)

| Chemical Name | Actual Weight % | Actual Weight % |
|---|---|---|
| D.I. Water | 39.00 | 29.00 |
| Jaguar Excell | 0.10 | 0.10 |
| Sodium C14–C16 Olefin Sulfonate | 35.00 | 35.00 |
| Lauramine oxide 29% | 3.70 | 3.70 |
| Lauryl alcohol | 5.00 | 5.00 |
| DC-1870 HV | 5.12 | 5.12 |
| Silicone microemulsion SME 253 | 1.00 | 1.00 |
| DI water | 9.00 | 9.00 |
| DMDM Hydantoin 55% | 0.10 | 0.10 |
| Hydrogen peroxide, 35% | 10.00 | 20.00 |
| Sodium Chloride | 2.20 | 2.20 |
| Fragrance | 0.20 | 0.20 |
| Phosphoric acid, 85% | 0.60 | 0.60 |
| Specification: pH =2.7 to 3.0 Viscosity = 3000 to 6000 cps (spindle#4, 20 rpm) | | |

Embodiments of the above invention have been described in order to illustrate the invention. It will be appreciated that one skilled in the art could make modifications to the above embodiments without deviating from the spirit and scope of the present invention.

What is claimed is:

1. A method for permanently dyeing hair which comprises subjecting said hair to a number of treatments, having a set time interval between each two consecutive such treatments, wherein each treatment comprises:

a.) contacting said hair for a period of about 5 seconds to about 2 minutes with a recently made mixture of:

part ai: oxidative dye intermediates in a shampoo base at alkaline pH; and wherein part ai optionally has about 0.01 to about 5% of a conditioning agent and optionally has about 0.01 to about 10% of a structurant;

part aii: an oxidative compound in a shampoo base at acidic pH and wherein part aii optionally has about 0.01 to about 5% of a conditioning agent; and optionally has about 0.01 to about 10% of a structurant;

with the proviso that at least one of part ai and part aii has about 0.01 to about 5% of a conditioning agent;

and at least one of part ai and part aii optionally has about 0.01 to about 10% of a structurant b.) rinsing said mixture from said hair with water;
and wherein said number of treatments with an identically formulated mixture is at least 6 or more; and wherein said set time interval between each two consecutive treatments is between about 8 hours and 30 days.

2. A method according to claim 1, wherein said dye intermediate is selected from the group consisting of:

m-aminophenol;
p-phenylene diamine;
p-toluenediamine;
2-chloro-p-phenylenediamine;
N-phenyl-p-phenylenediamine
N-2-methoxyethyl-p-phenylenediamine;
N,N-bis-(hydroxyethyl)-p-phenylenediamine;
2-hydroxymethyl-p-phenylenediamine
2-hydroxyethyl-p-phenylenediamine;
4, 4'-diaminodiphenylamine
2,6-dimethyl-p-phenylenediamine;
2-isopropyl-p-phenylenediamine;
N-(2-hydroxypropyl)-p-phenylenediamine;
2-propyl-p-phenylenediamine;
1,3-N, N-bis-(2-hydroxyethyl)-N, N-bis (4-aminophenyl)-2-propanol;
2-methyl-4-dimethylaminoaniline;
p-aminophenol;
p-methylaminophenol;
3-methyl-p-aminophenol;
2-hydroxymethyl-p-aminophenol;
2-methyl-p-aminophenol;
2-(2-hydroxyethylaminomethyl)-p-aminophenol;
2-methoxymethyl-p-aminophenol;
5-aminosalicylic acid;
catechol;
pyrogallol;
o-aminophenol;
2, 4-diaminophenol;
2,4,5-trihydroxytoluene;
1,2,4-trihydroxybenzene;
2-ethylamino-p-cresol;
2,3-dihydroxynaphthalene;
5-methyl-o-aminophenol;
6-methyl-o-aminophenol;
2-amino-5-acetaminophenol;
2-methyl-1-naphthol;
1-acetoxy-2-methylnaphthalene;
1,7-dihydroxynaphthalene;
resorcinol;
4-chlororesorcinol;
1-naphthol;
1,5-dihydroxynaphthalene;
2,7-dihydroxynaphthalene;
2-methylresorcinol;
1-hydroxy-6-aminonaphthalene-3-sulfonic acid;
thymol (2-isopropyl-5-methylphenol);
1,5-dihydroxy-1,2,3,4-tetrahydronaphthalene;
2-chlororesorcinol;
2,3-dihydroxy-1,4- naphthoquinone;
1-naphthol-4-sulfonic acid;
m-phenylenediamine;
2-(2,4-diaminophenoxy)ethanol;
N,N-bis(hydroxyethyl)-m-phenylenediamine;
2,6-diaminotoluene;
N,N-bis(hydroxyethyl)-2,4-diaminophenetole;
bis(2,4-diaminophenoxy)-1,3-propane;
1-hydroxyethyl-2,4-diaminobenzene;
2-amino-4-hydroxyethylaminoanisole;
aminoethoxy-2,4-diaminobenzene;
2,4-diaminophenoxyacetic acid;
4,6-bis(hydroxyethoxy)-m-phenylenediamine;
2,4-diamino-5-methylphenetole;
2,4-diamino-5-hydroxyethoxytoluene;
2,4-dimethoxy 1,3-diaminobenzene;
2,6-bis(hydroxyethylamino) toluene;
2-hydroxy-4-carbamoylmethylaminotoluene;
m-carbamoylmethylaminophenol;
6-hydroxybenzomorpholine;
2-hydroxy-4-aminotoluene;
2-hydroxy-4-hydroxyethylaminotoluene;
4,6-dichloro-m-aminophenol;
2-methyl-m-aminophenol;
2-chloro-6-methyl-m-aminophenol;
2-hydroxyethoxy-5-aminophenol;
2-chloro-5-trifluoroethylaminophenol;
4-chloro-6-methyl-m-aminophenol;
N-cyclopentyl-3-aminophenol;
N-hydroxyethyl-4-methoxy-2-methyl-m-aminophenol
5-amino-4-methoxy-2-methylphenol;
2-dimethylamino-5-aminopyridine
2,4,5,6-tetra-aminopyrimidine;
4,5-diamino-1-methylpyrazole;
1-phenyl-3-methyl-5-pyrazolone;
6-methoxy-8-aminoquinoline;
2,6-dihydroxy-4-methylpyridine;
5-hydroxy-1,4-benzodioxane;
3,4-methylenedioxyphenol;
4-hydroxyethylamino-1,2-methylenedioxybenzene;
2,6-dihydroxy-3,4-dimethylpyridine;
5-chloro-2,3-dihydroxypyridine;
3,5-diamino-2,6-dimethoxypyridine;
2-hydroxyethylamino-6-methoxy-3-aminopyridine;
3,4-methylenedioxyaniline;
2,6-bis-hydroxyethoxy-3,5-diaminopyridine;
4-hydroxyindole;
3-amino-5-hydroxy-2,6-dimethoxypyridine,
5,6-dihydroxyindole;
7-hydroxyindole;
5-hydroxyindole;
2-bromo-4,5-methylenedioxyphenol;
6-hydroxyindole;
3-amino-2-methylamino-6-methoxypyridine;
2-amino-3-hydroxypyridine;

2,6-diaminopyridine;

5-(3,5-diamino-2-pyridyloxy)-1,3-dihydroxypentane;

3-(3,5-diamino-2-pyridyloxy)-2-hydroxypropanol 4-hydroxy-2,5,6-triaminopyrimidine;

or combinations thereof.

3. A method according to claim 1, wherein said part ai prior to mixture with said part aii, has a pH of about 8 to about 11.

4. A method according to claim 1, wherein said part ai, prior to mixture with said part ai has a pH of about 3 to about 4.

5. A method according to claim 1 wherein said period for contacting said hair is between about ½ minute and about 2 minutes.

6. A method according to claim 1 wherein said set time interval is between about 1 day and about 3 days.

7. A method according to claim 1 wherein said hair is highlighted.

8. A method according to claim 1 wherein said hair has a yield stress index in the range of about 200 to 1500.

9. A method according to claim 1 wherein said hair has a yield stress index in the range of about 400 to 1500.

10. A method according to claim 1 wherein said hair has a yield stress index in the range of about 800 to 1500.

11. A method according to claim 1 wherein said hair has a combing index in the range of about 1.1 to about 4.0.

12. A method according to claim 1 wherein said hair has a combing index in the range of about 1.2 to about 3.5.

13. A method according to claim 1 wherein said hair has a combing index in the range of about 1.5 to about 3.0.

14. A method according to claim 1 wherein said method minimizes hair outgrowth.

15. A method according to claim 1 wherein said hair has a combing force of about 5 to about 55 gmforce.

16. A method according to claim 1 wherein said hair has a combing force of about 10 to about 20 gmforce.

17. A method according to claim 1 wherein said hair has a combing force of about 10 to about 16 gmforce.

18. A method according to claim 1 wherein said method minimizes hair color fading.

19. A method according to claim 1 wherein said hair minimize root outgrowth.

20. A method according to claim 1 wherein said mixture of part ai and part aii delivers delta E of about 0.1 to about 65 on blonde hair and delta E of about 0.1 to about 8 on brown hair.

21. A method according to claim 1 wherein said method delivers to said hair a ratio IR absorption at 1040/1240 of about 0.01 to 1.5.

22. A method according to claim 1 wherein said method delivers to said hair a ratio IR absorption at 1040/1240 of about 0.01 to 1.0.

23. A method according to claim 1 wherein said method delivers to said hair a ratio IR absorption at 1040/1240 of about 0.01 to 0.5.

24. A method according to claim 1 wherein said oxidative compound is selected from the group consisting of hydrogen peroxide, urea peroxide, melamine peroxide, sodium perborate, sodium percarbonate, and mixtures thereof.

25. A method according to claim 1 wherein part ai comprises from about 35% to about 98.9% water.

26. A method according to claim 1, wherein the mixture of part ai and part aii has a neat viscosity of from about 500 cps to about 60,000 cps at 26.7 degree. C., as measured by a Brookfield RVTDCP with a spindle CP-41 at 1 RPM for 3 minutes.

27. A method in accordance with claim 1, wherein said hair has a break stress of about 0.005 to about 0.03 gmforce/micron.

28. A method in accordance with claim 1, wherein said hair has a break stress of about 0.005 to about 0.025 gmforce/micron.

29. A method in accordance with claim 1, wherein said hair has a break stress of about 0.005 to about 0.018 gmforce/micron.

30. A method according to claim 1 wherein said oxidative hair colorant is present at about 0.1% to about 10%.

31. A method according to claim 1 wherein said oxidative dye intermediates are present at about 2% to about 5%.

32. A dispenser for dispensing simultaneously part ai and part aii according to claim 1, which comprises:
  A.) a means for holding part ai and part aii in physically separate locations;
  B.) a means for protecting part ai and part aii from air prior to dispensing;
  C.) a means for dispensing part ai and part aii in equal amounts and in proximity to each other.

33. A method according to claim 1 wherein part ai and part aii are mixed by hand.

34. A method according to claim 1 which comprises rinsing said mixture of part ai and part aii from said hair with water in a shower.

* * * * *